(12) United States Patent
Keranen

(10) Patent No.: US 9,476,707 B2
(45) Date of Patent: Oct. 25, 2016

(54) METHOD AND MEASURING DEVICE FOR MEASURING THE DISTANCE OF A SURFACE, THICKNESS AND OPTICAL PROPERTIES OF AN OBJECT

(71) Applicant: FOCALSPEC OY, Oulu (FI)

(72) Inventor: Heimo Keranen, Oulu (FI)

(73) Assignee: FOCALSPEC OY, Oulu (FI)

( * ) Notice: Subject to any disclaimer, the term of this patent is extended or adjusted under 35 U.S.C. 154(b) by 0 days.

(21) Appl. No.: 14/427,127

(22) PCT Filed: Sep. 17, 2013

(86) PCT No.: PCT/FI2013/050898
§ 371 (c)(1),
(2) Date: Mar. 10, 2015

(87) PCT Pub. No.: WO2014/041254
PCT Pub. Date: Mar. 20, 2014

(65) Prior Publication Data
US 2015/0219454 A1   Aug. 6, 2015

(30) Foreign Application Priority Data
Sep. 17, 2012  (FI) ................... 20125958

(51) Int. Cl.
*G01C 3/08* (2006.01)
*G01N 21/57* (2006.01)
(Continued)

(52) U.S. Cl.
CPC ............ *G01C 3/08* (2013.01); *G01B 9/02091* (2013.01); *G01B 11/0633* (2013.01);
(Continued)

(58) Field of Classification Search
CPC  G01C 3/08; G01B 9/02091; G01B 11/0633; G01B 11/0691; G01B 2210/50; G01N 21/47; G01N 21/4795; G01N 21/8422
See application file for complete search history.

(56) References Cited

U.S. PATENT DOCUMENTS

| 5,880,846 A | 3/1999 | Hasman et al. |
| 2002/0075484 A1 | 6/2002 | Cohen-Sabban |

(Continued)

FOREIGN PATENT DOCUMENTS

| EP | 0183240 A2 | 6/1986 |
| EP | 0890822 A2 | 1/1999 |

(Continued)

OTHER PUBLICATIONS

International Search Report, dated Jan. 29, 2014, from corresponding PCT application.

(Continued)

*Primary Examiner* — Luke Ratcliffe
*Assistant Examiner* — Samantha K Abraham
(74) *Attorney, Agent, or Firm* — Young & Thompson

(57) ABSTRACT

In the measuring device and measuring method, confocal measuring principle is utilized. A certain component of an optical measurement signal is, from the point of view of both illumination and imaging, in focus only at one point on the virtual measuring surface. In the measuring device, the surface to be measured always hits a common focus point of the illumination and imaging, whereby a reflection is generated. The reflected optical signal is directed to a detector belonging to the imaging unit, where one picture element of the detector corresponds to a certain focus point, respectively. The optical efficiency received by each picture element is indicated. The light reflecting from the intersection of the virtual measuring surface and the surface of the object produces an intensity maximum for the detector. This maximum point is indicated and converted in the imaging unit (13) into the height of the surface of the object.

20 Claims, 11 Drawing Sheets

Figure 1A:
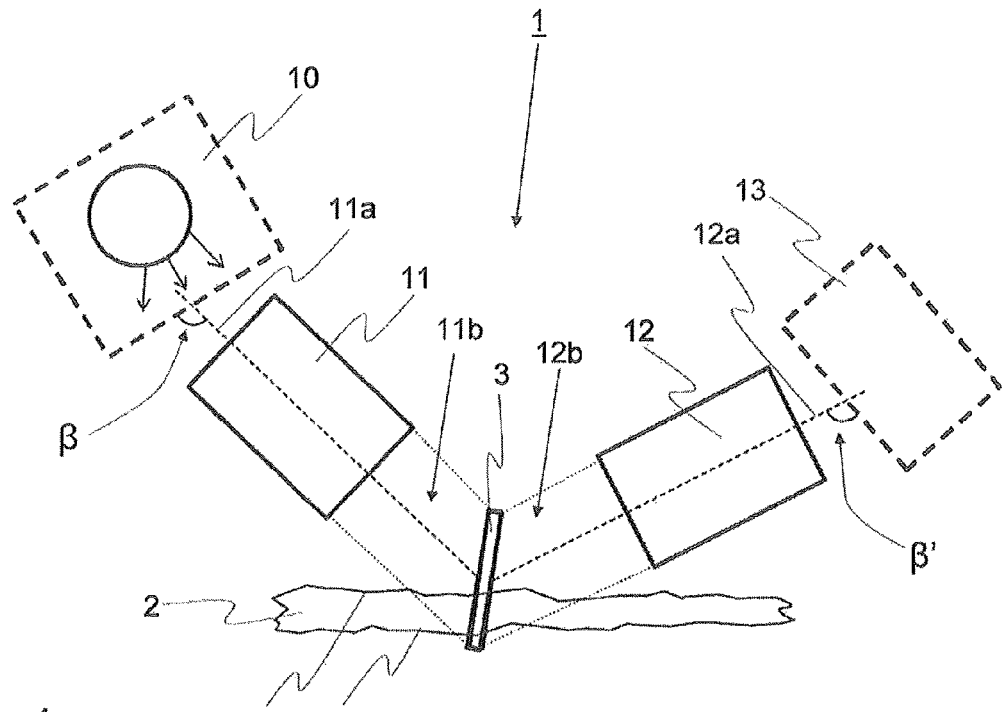

(51) Int. Cl.
*G01N 21/47* (2006.01)
*G01N 21/84* (2006.01)
*G01B 11/06* (2006.01)
*G01B 9/02* (2006.01)
*G01N 21/49* (2006.01)

(52) U.S. Cl.
CPC ......... *G01B 11/0691* (2013.01); *G01N 21/47* (2013.01); *G01N 21/57* (2013.01); *G01N 21/8422* (2013.01); *G01B 2210/50* (2013.01); *G01N 21/49* (2013.01)

(56) References Cited

U.S. PATENT DOCUMENTS

| | | | |
|---|---|---|---|
| 2004/0145753 A1* | 7/2004 | Lim | G01B 11/2509 356/602 |
| 2005/0225752 A1* | 10/2005 | Takai | G01N 21/4795 356/237.1 |
| 2006/0077385 A1* | 4/2006 | Wang | G01J 3/02 356/328 |
| 2008/0137061 A1 | 6/2008 | Rush | |
| 2012/0019821 A1* | 1/2012 | Chen | G02B 21/0032 356/303 |
| 2012/0206710 A1 | 8/2012 | Niemela et al. | |

FOREIGN PATENT DOCUMENTS

| | | |
|---|---|---|
| EP | 1715290 A1 | 10/2006 |
| EP | 1855082 A1 | 11/2007 |
| EP | 2124085 A1 | 11/2009 |
| FR | 2848664 A1 | 6/2004 |
| GB | 2043389 A | 10/1980 |
| JP | 2007147299 A | 6/2007 |
| WO | 2008046966 A1 | 4/2008 |

OTHER PUBLICATIONS

Finland Search Report, dated May 6, 2013, from corresponding Finnish application.

Taphanel M. et al., "Fast 3D in-line sensor for specular and diffuse surfaces combining the chromatic confocal and triangulation principle", Proceedings of IEEE International Instrumentation and Measurement Technology Conference, pp. 1072-1077 (May 13, 2012).

European Search Report, dated Jan. Mar. 17, 2016, from corresponding application EP 13837251.1.

Lin P. C. et al: "Single-shot depth-section imaging through chromatic slit-scan confocal microscopy", Applied Optics, Optical Society of America, Washington. DC; US. vol. 37. No. 28. Oct. 1, 1998. pp. 6764-6770. XP002220147.

* cited by examiner

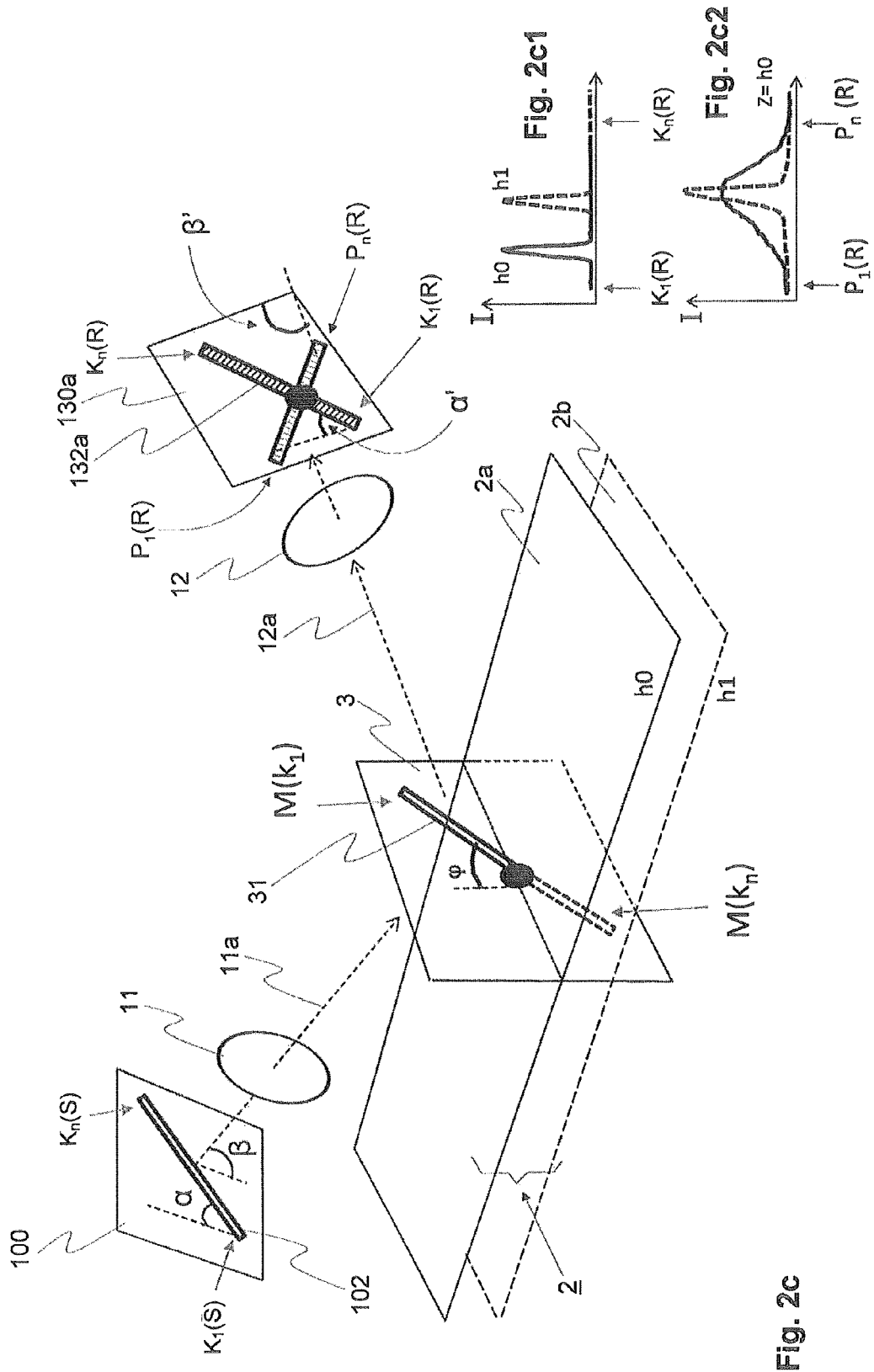

METHOD AND MEASURING DEVICE FOR MEASURING THE DISTANCE OF A SURFACE, THICKNESS AND OPTICAL PROPERTIES OF AN OBJECT

BACKGROUND OF THE INVENTION

The invention relates to a measuring method and equipment for determining the level, thickness and optical properties of an object to be measured with an optical measuring device.

In industrial processes there is a need to measure relief of surface of a product or its thickness as a measurement connected to the production process. Thereby, the product being the object of the measurement, for example, a film-like material moves by the measuring point. Examples of this kind of products include paper, rolled metal band or a plastic film. In manufacturing processes of all these products, the measuring of the relief of surface of the product can be performed, for example, mechanically by a sensor contacting the surface. A sensor contacting the surface can, however, damage the surface in a way that is not allowed by the end user.

Therefore, different electrical and optical measuring devices have been developed. In an optical measurement of surface, chromatic aberration can be used. In this kind of a measuring system, light is focused onto the surface to be measured through an optical element, the focal length of which depends in a known way on the wavelength of the light. The light reflected from the surface is collected either with the same optical element used for illumination or with another optical element to a detector. The wavelengths of the signal received by the detector are analysed and the spectral part that received the strongest signal is indicated. When it is known where the focus is in the measuring system, the location of the reflection point can be determined.

DESCRIPTION OF THE RELATED ART

Measuring of the height of surface is disclosed to be performed by the above-described method in publications US 2012206710 and WO 2008046966.

In publication JP 2007147299 a measuring method is disclosed, whereby a point of the illumination element is imaged with a lens having chromatic aberration into a line in direction of the optical axis, whereby in different places a different wavelength is in focus. The reflection caused by this line of the surface to be measured is imaged for the sensor element with optics that hasn't got chromatic aberration. In a solution according to the reference the measuring plane (=a line dispersed into a spectrum) can not be perpendicular to the surface to be measured. As the level of the surface changes, the measurement point on the surface of the object moves either to the receiver or the sender. Thereby, with the change of the height of surface to be measured, the illumination angle and imaging arrangement do not remain equal compared with each other.

In laser triangle measuring the place of the dotted or linear laser line changes according to the distance of the object to be measured. In the method, the object is illuminated by laser and the laser light is refracted from the surface. The point of the reflected light on the sensor corresponds to a certain level of surface. If the object is transparent, then a separate reflection is obtained from both of the interfaces. The points of reflections on the sensor represent, in this case, the thickness of the object.

Surface contour of an object can also be measured by optical coherent tomography (OCT). In the method, measuring of the surface contour is based on interference figure of light obtained with laser as it meets the surface to be measured.

SUMMARY OF THE INVENTION

The object of the invention is to disclose an optical measuring arrangement and a measuring method, where the level or thickness of the surface of the object or the optical properties of the object are measured optically by using confocal principle.

The objects of the invention are achieved by an optical measuring device, measuring arrangement and measuring method, where the geometric shape of the light area utilized in illuminating is focused by means of illumination optics onto a virtual measuring surface that intersects the surface of the object to be measured. For the same virtual measuring surface there is in focus also imaging optics that receives the light reflected and/or scattered from the surface of the object to be measured. Of the received light is detected with a position-sensitive detector an intensity profile where a signal maximum provided by the reflection point can be found that is calibrated to correspond to the height of the reflection point in the object to be measured. In order to define the optical properties of the surface of the object, in the defined maximum reflection object also the intensity profile of the received light in perpendicular direction in respect of the measuring axis of the position measurement is measured.

An advantage of the invention is that the optics of the measuring device is simple and inexpensive as to its structural parts.

Further, an advantage of the invention is that in the measurement, the depth of field of focus of illumination and imaging is arbitrary small, for example, some micrometers, even if the range of distance is, for example, ten millimeters.

Further, an advantage of the invention is that in the invention, maximal luminosity can be utilized, since the angular space of both the illumination and imaging is large. A large angular space enables measuring of shiny surfaces in a large angular range.

Further, an advantage of the invention is that is a completely optical and nonsurface-contacting measuring device that is able to measure simultaneously several measurement points with a resolution of parts of micrometers also in very quickly moving objects.

Further, it is an advantage of the invention that it is suitable also for matte, shiny and transparent materials.

Further, an advantage of the invention is that measuring of the thickness of transparent pieces can be performed from one side of the surface to be measured.

Further, an advantage of the invention is that by means of it, quality control measurements traditionally performed in a laboratory can be realized in real-time directly on a process line, whereby measurement data can be used in adjusting the process.

An optical measuring device of height of surface according to the invention, comprising
   an optical light source
   illumination optics that directs light of the light source to the object to be measured
   imaging optics that is configured to collect reflected or scattered light from the object of measuring to the imaging unit imaging unit that is configured to indicate the intensity distribution of the light coming from the object of measuring, is characterized in that the light source consists of one or more line-like optical output elements or dotted optical output elements on a output element (100), the optical output elements being configured to produce light at least on one wavelength the imaging unit comprises a light sensor that consists of one or more line-like, dotted or region-like detector areas that include one corresponding point for an individual point of the optical output element of the light source, the imaging unit being configured to define the intensity value of light at least for a part of the corresponding points and to define the location of the surface to be measured even from the location of the maximum intensity of light in the detector area, and that illumination optics and imaging optics are configured to form a common focus point on the virtual measurement surface such that on the virtual measurement surface the image formed by the illumination optics from the point of the optical output element is overlapping with the image formed by the imaging optics from the corresponding point of the detector at least on one common wavelength or aperture angle of the illuminator optics or imaging optics.

An optical measuring device of thickness comprising a first optical measuring device for measuring of a first surface, and a second optical measuring device for measuring a second surface, is characterized in that the first measuring device is configured to measure the height of the top surface of the object, and the second measuring device is configured to measure the height of the bottom surface of the object, and that the difference between the measurement results is configured to be indicated in a measurement arrangement as thickness of the object.

The optical measuring method of height of surface, whereby the optical illumination and optical imaging of the surface of the object is performed biaxially such that both the illumination and imaging are directed to the surface from different directions, is characterized in that the imaging and the illumination are realized confocally onto a virtual measuring surface that intersects the surface of the object, and that the level of the object is indicated at the place of the intensity maximum of the light reflected from the surface of the object received by the imaging unit in the image sensor of the imaging unit that includes one corresponding point for an individual point of the optical output element of the light source.

Some advantageous embodiments of the invention are disclosed in the dependent claims.

The basic idea of the invention is the following: The invention comprises an optical arrangement where a surface is illuminated by an illumination arrangement and imaged by a separate imaging arrangement. Illumination and imaging are realized biaxially so that the illumination is directed to the surface from a different direction than the imaging. In the illumination arrangement, with a light source an output element is illuminated that can comprise either an output slit/slits or a wavelength band filter (Linear Variable Filter; LVF) for providing a light region. A light region can also be provided by different light components fixed to the output element, such as LEDs. The appearance of the light area created by the output slits, wavelength band filter or LEDs is focused onto the virtual measuring surface that intersects the surface of the object to be measured. The same virtual measuring surface is imaged from the other direction with imaging optics, the focus points of which are located also on said virtual measuring surface. The virtual measuring surface may comprise points of the surface, a set of lines on the surface or multiple measuring points on said surface. In the imaging arrangement, measurement signal reflected from a certain focus point common for illumination and imaging that is on the surface of the object to be measured. The level of the object is defined from the place of the intensity maximum included in the image data formatted for the image sensor by the imaging optics.

The focus points of the illumination and imaging arrangements are provided on the measuring surface intersecting the surface to be measured. The measuring surface can be a plane that can be perpendicular to the surface to be measured but this is, however, not essential. Imaging and illumination are realized confocally such that both the focus points of the illumination optics and the focus points formed by the imaging optics coincide on the virtual measuring surface in a way that an individual point of the light source region being in focus is focused to one corresponding point of the detector of the imaging optics. With this arrangement, the surface of the object to be measured always hits one of the several illumination optics of the optical arrangement according to the invention and of the common focus points for the imaging optics (confocal measuring principle). Reflection of the optical signal occurring in the focus point is multiple in comparison with other reflections occurring from the surface of the object that proceed through the imaging optics to the detector means. The place of the measuring signal reflected from the focus point is indicated by a light-sensitive sensor included in the imaging arrangement. The indicated place of the point on the sensor is calibrated to correspond to a certain level of the object to be measured.

In order to define the optical properties of the surface of the object advantageously at the defined point of maximum reflection also the intensity profile of the received light is measured in a direction deviating from the direction of the position measuring axis at least in one point. The shape of this intensity profile is determined by the characteristics of the surface of the object to be measured. From this profile, for example, the degree of gloss of the surface can be found out. The degree of gloss can be indicated, for example, by measuring the intensity of light in one or in several points outside the position measuring axis in the vicinity of the point of maximum reflection.

BRIEF DESCRIPTION OF THE DRAWING FIGURES

Figure 1B:
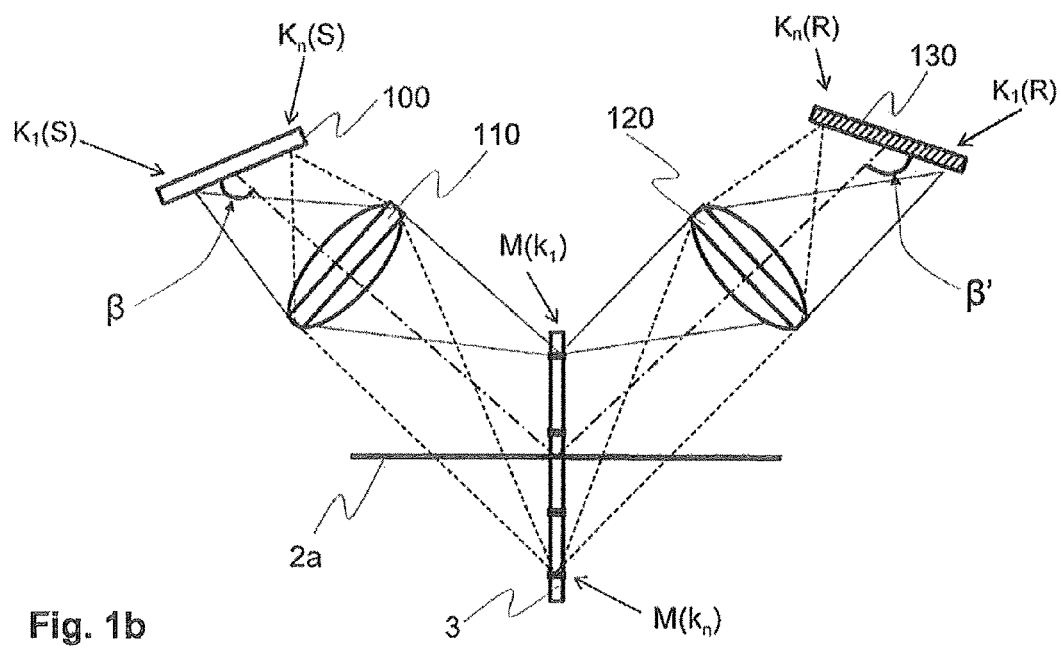
Figure 1C:
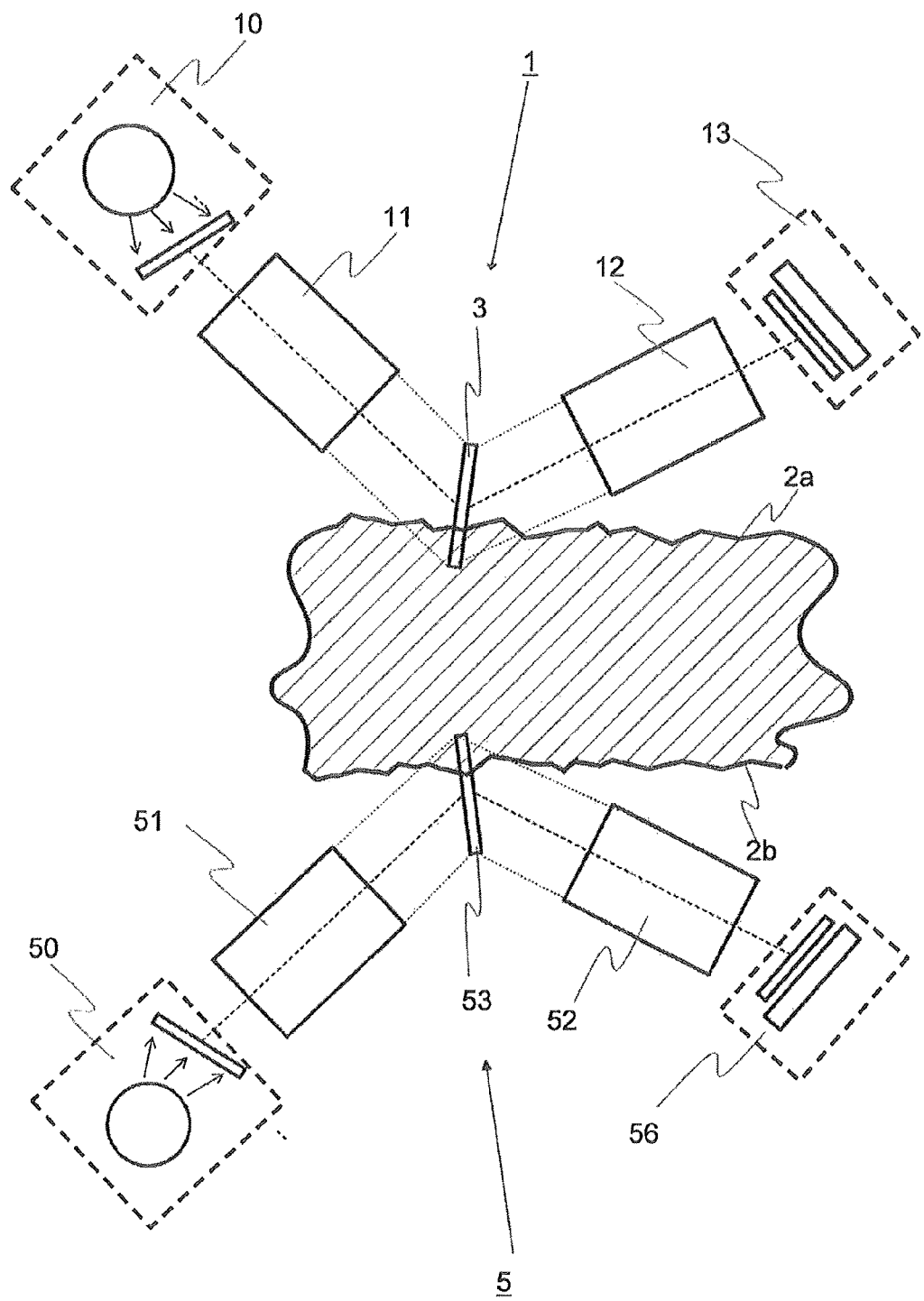

In the following, the invention will be described in detail. In the description, reference is made to the enclosed drawings, in which FIG. 1*a* shows by way of example a general structure of an optical measuring device according to the invention, FIG. 1*b* shows an example of the operating principle of an optical measuring device according to the invention, FIG. 1*c* shows in way of example applying of an optical measuring device according to the invention to measurement of thickness in a case where light does not transmit the object to be measured.

Figures 2A, 2B:
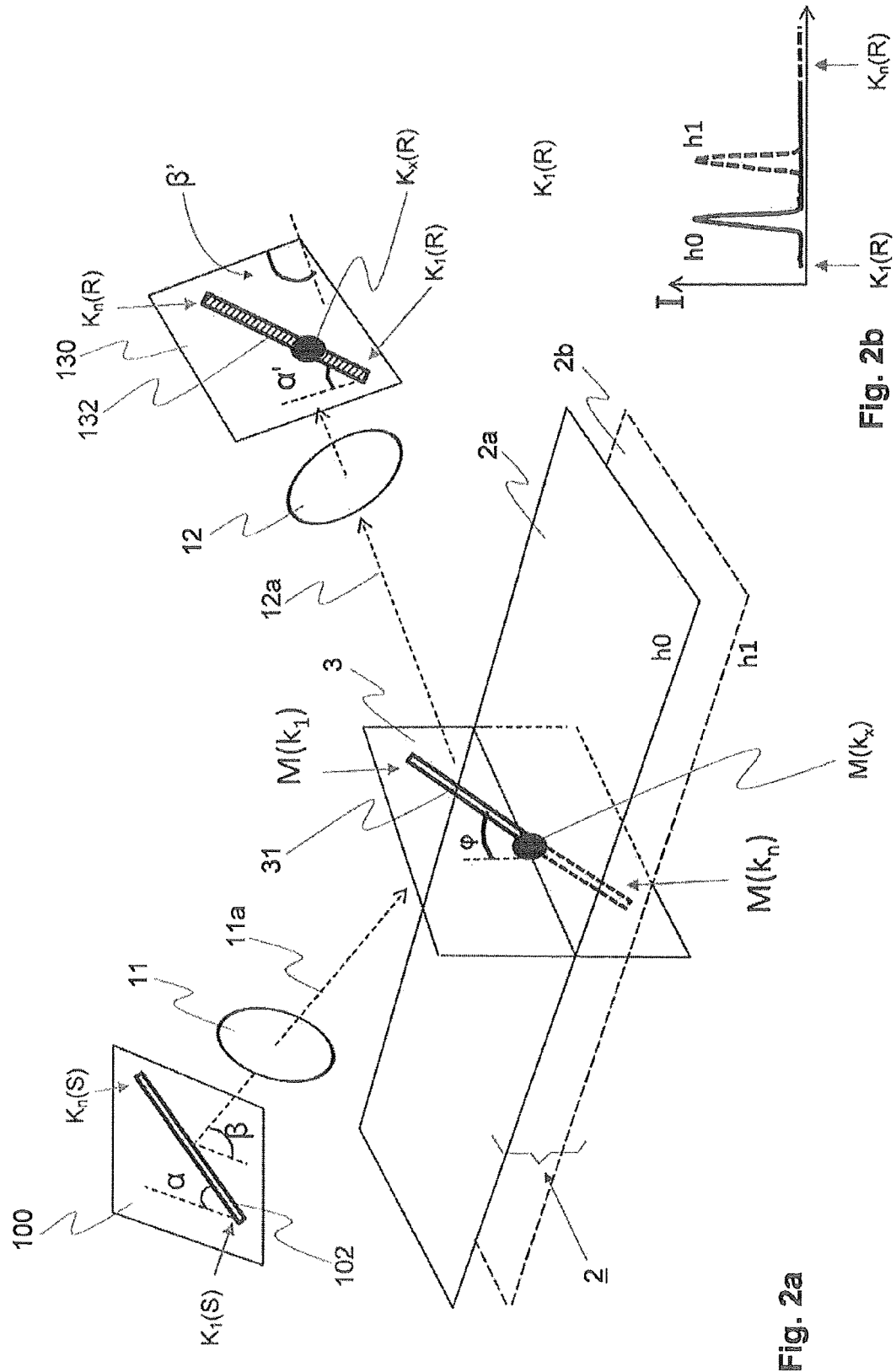
Figure 2D:
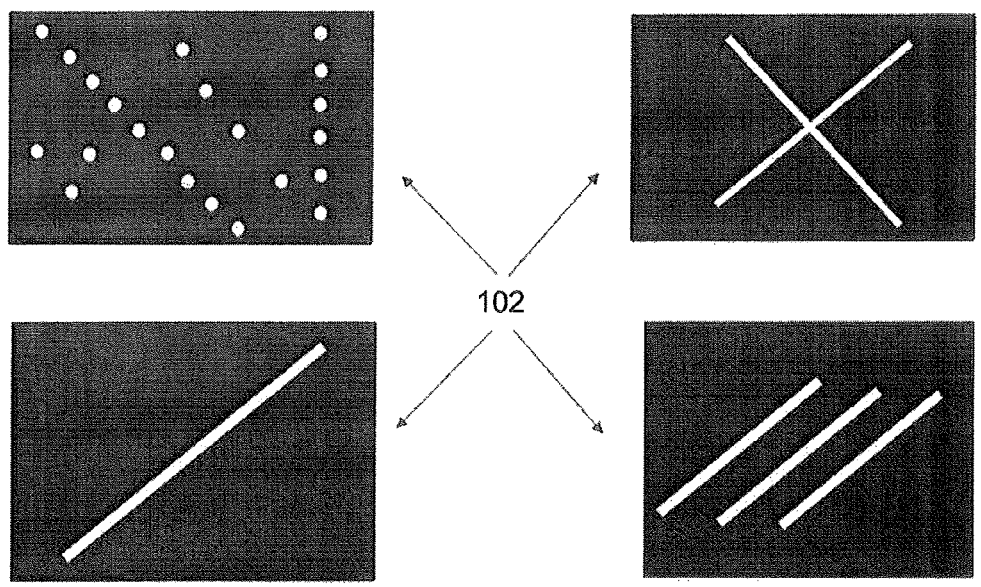
Figure 2E:
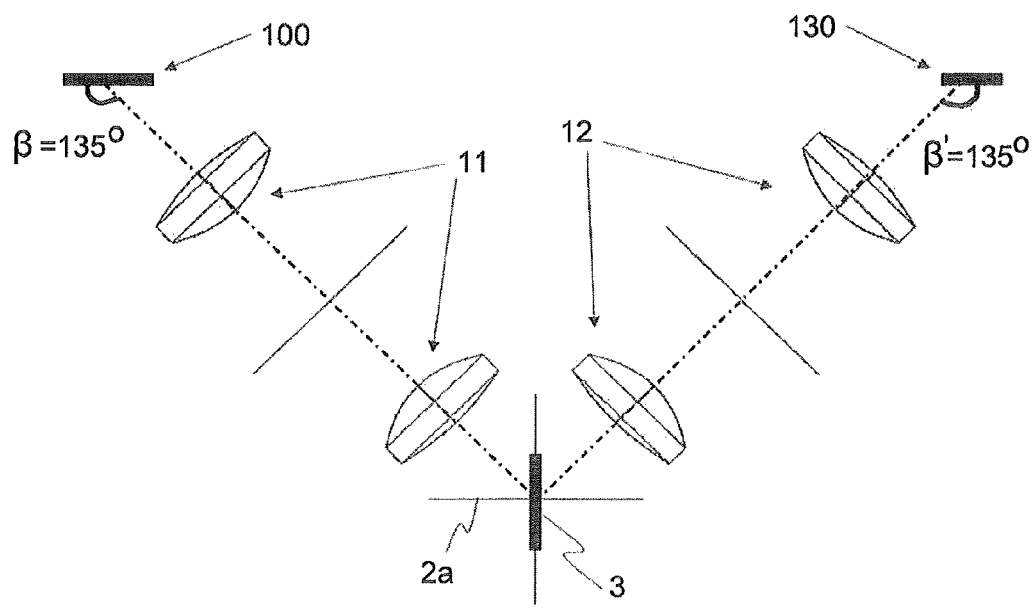
Figure 2F:
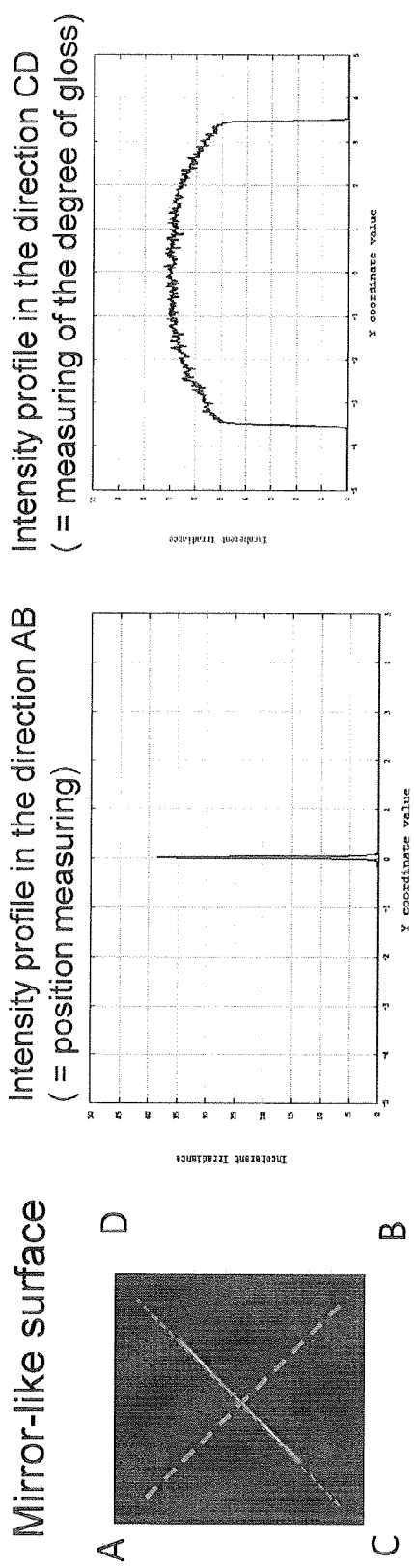
Figure 2F:
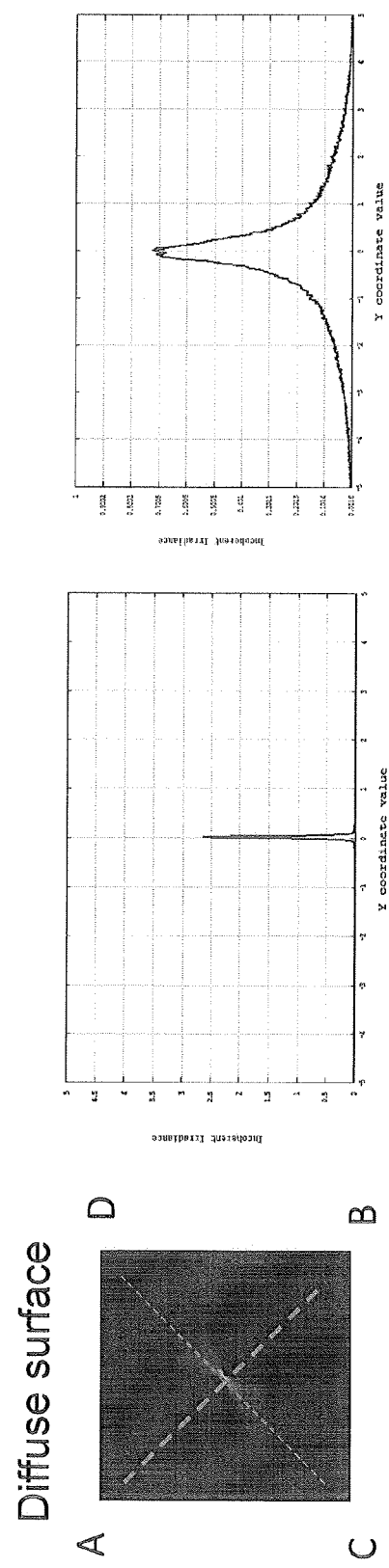
Figure 3:
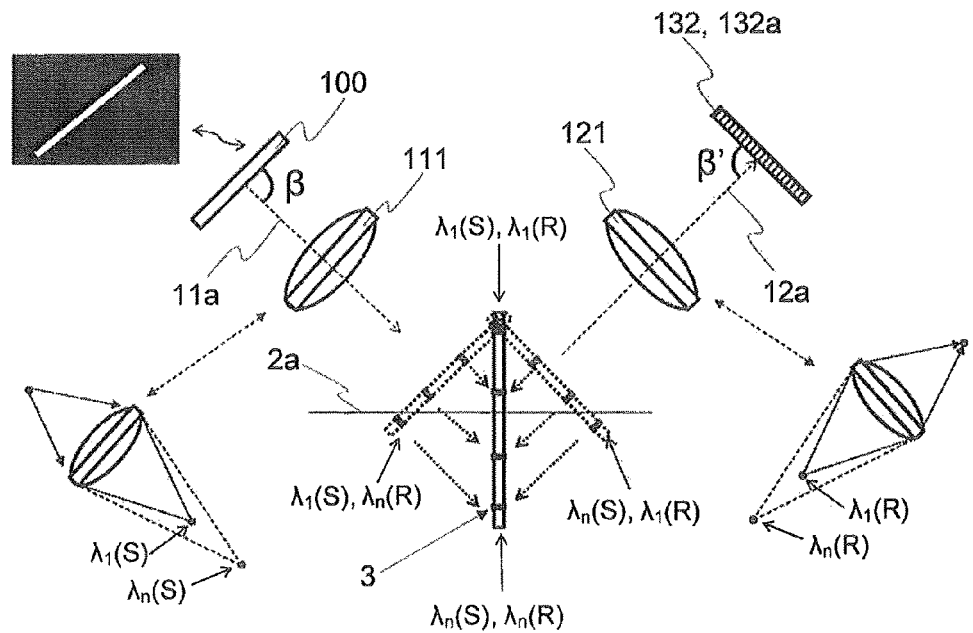
Figure 4:
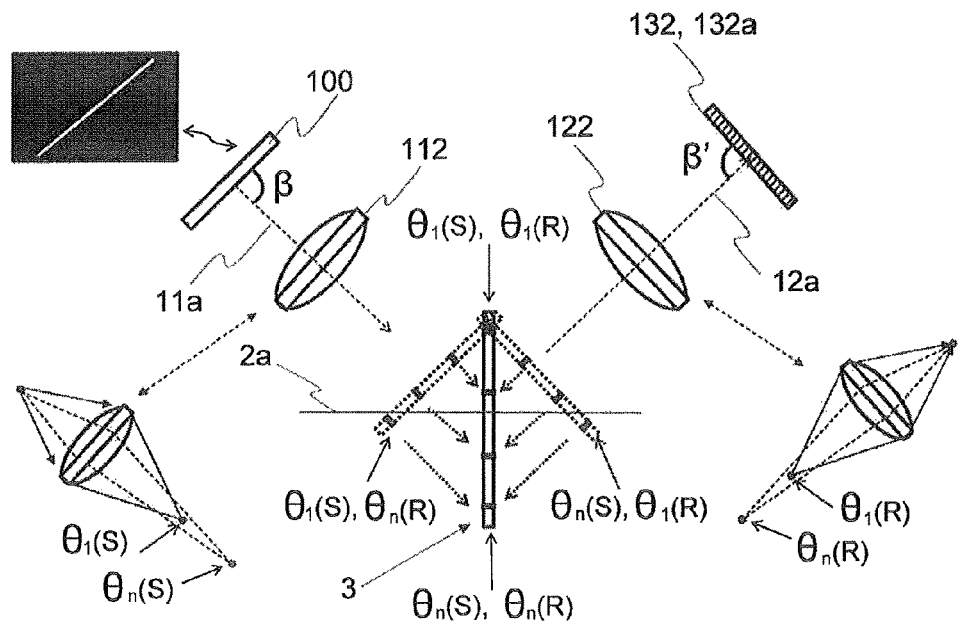
Figure 5A:
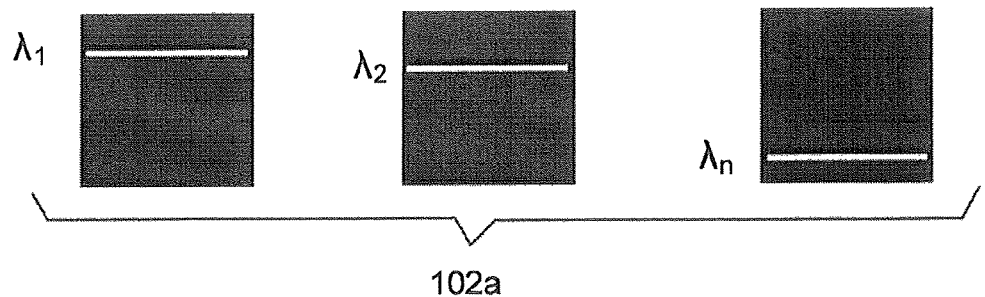
Figure 5B:
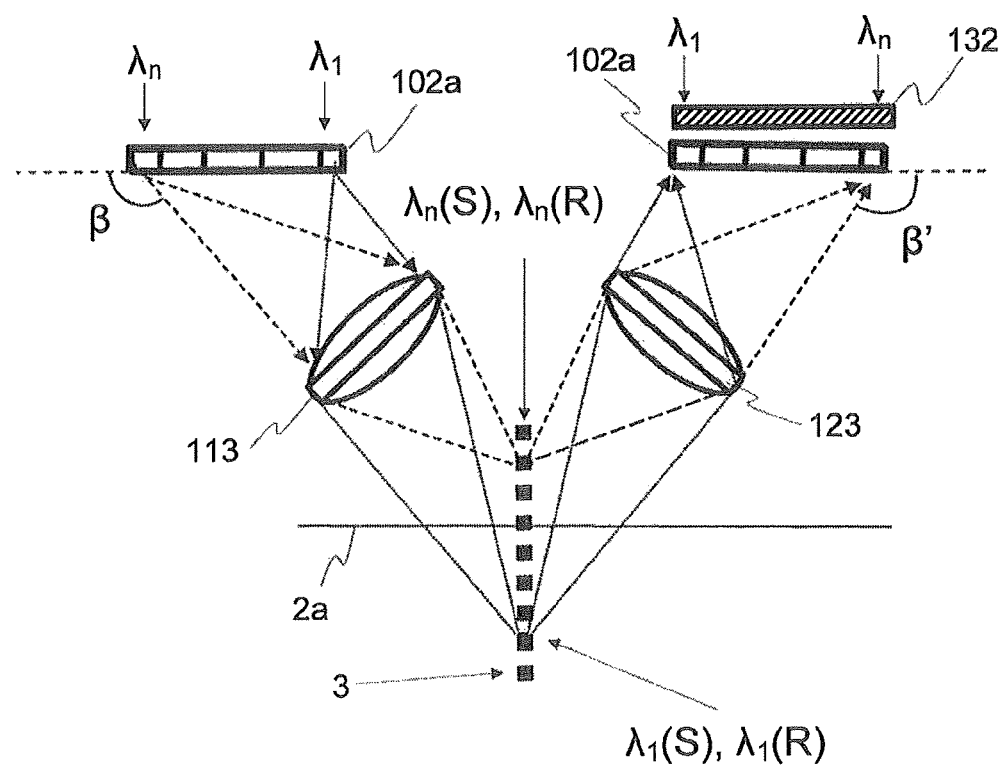
Figure 5C:
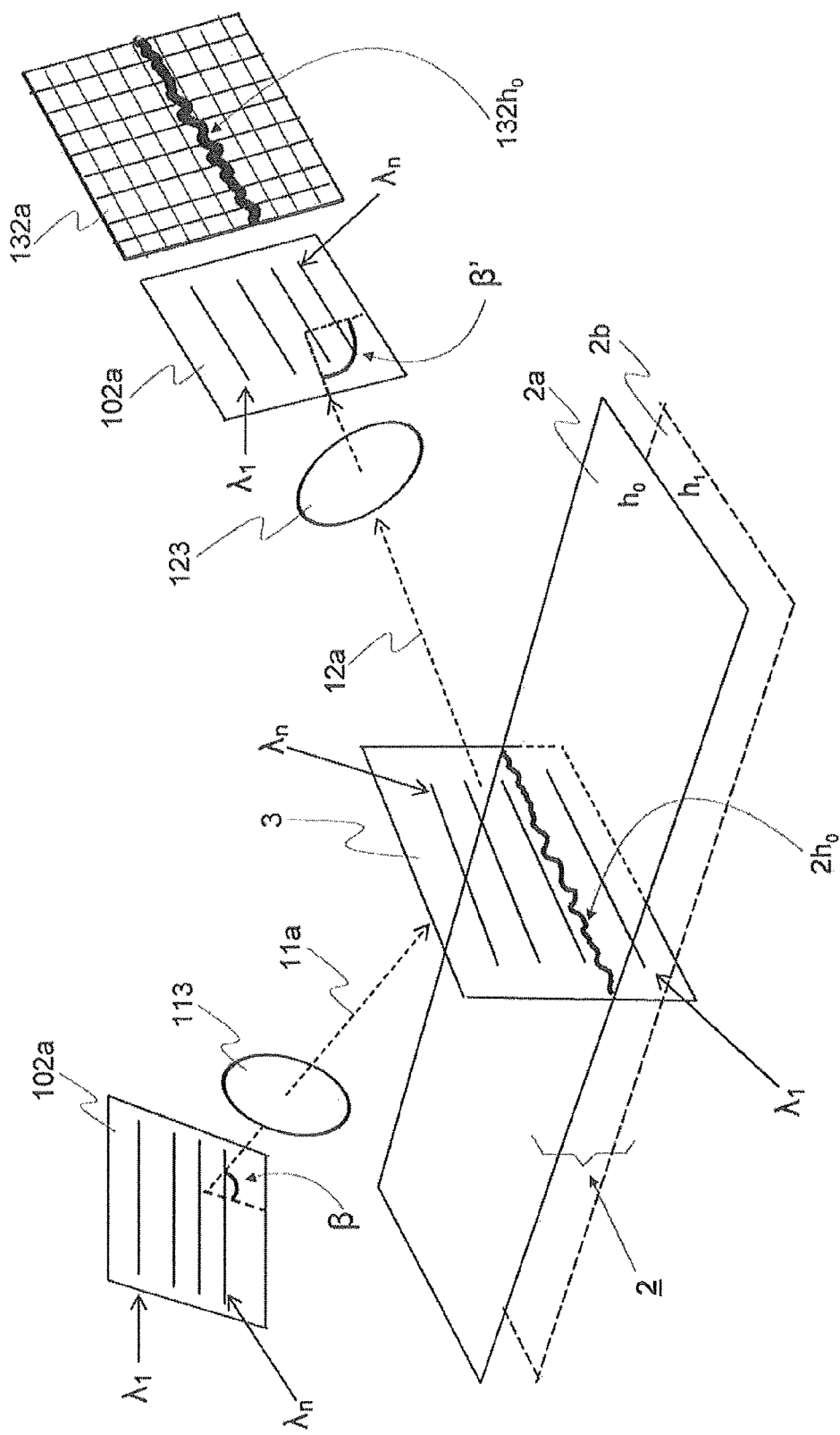
Figure 6A:
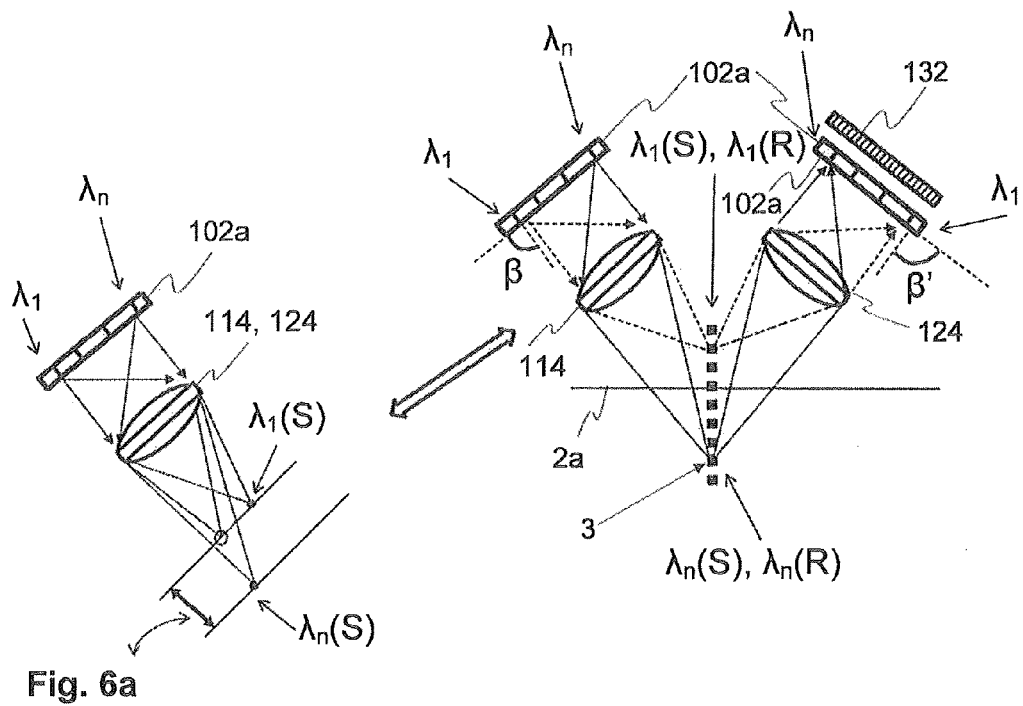
Figure 6B:
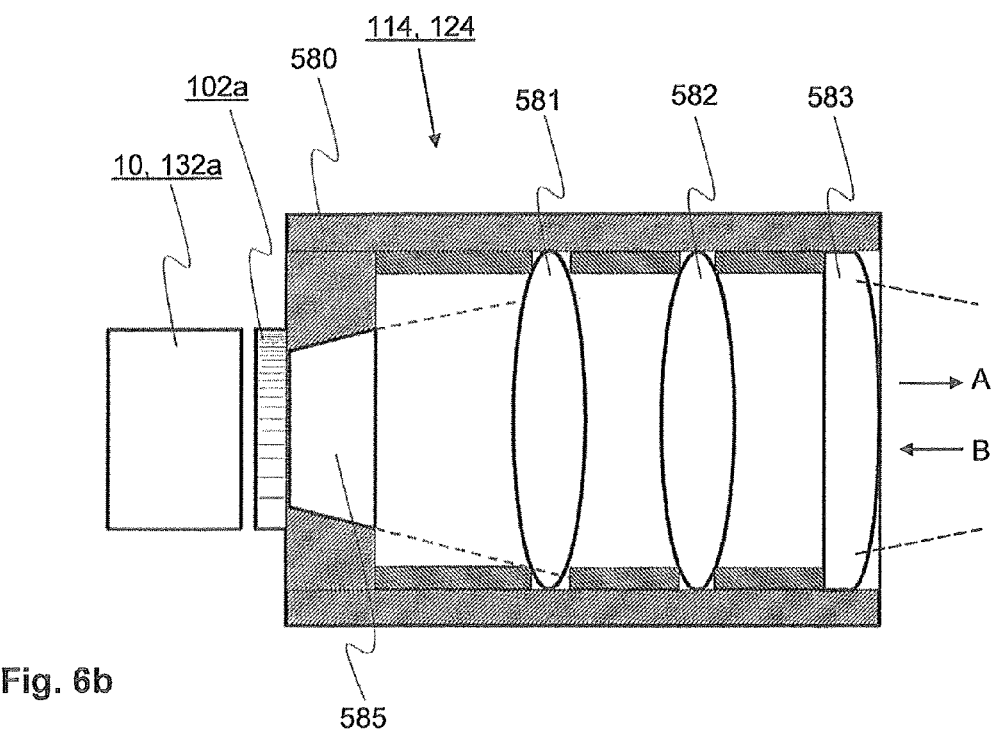
Figure 7:
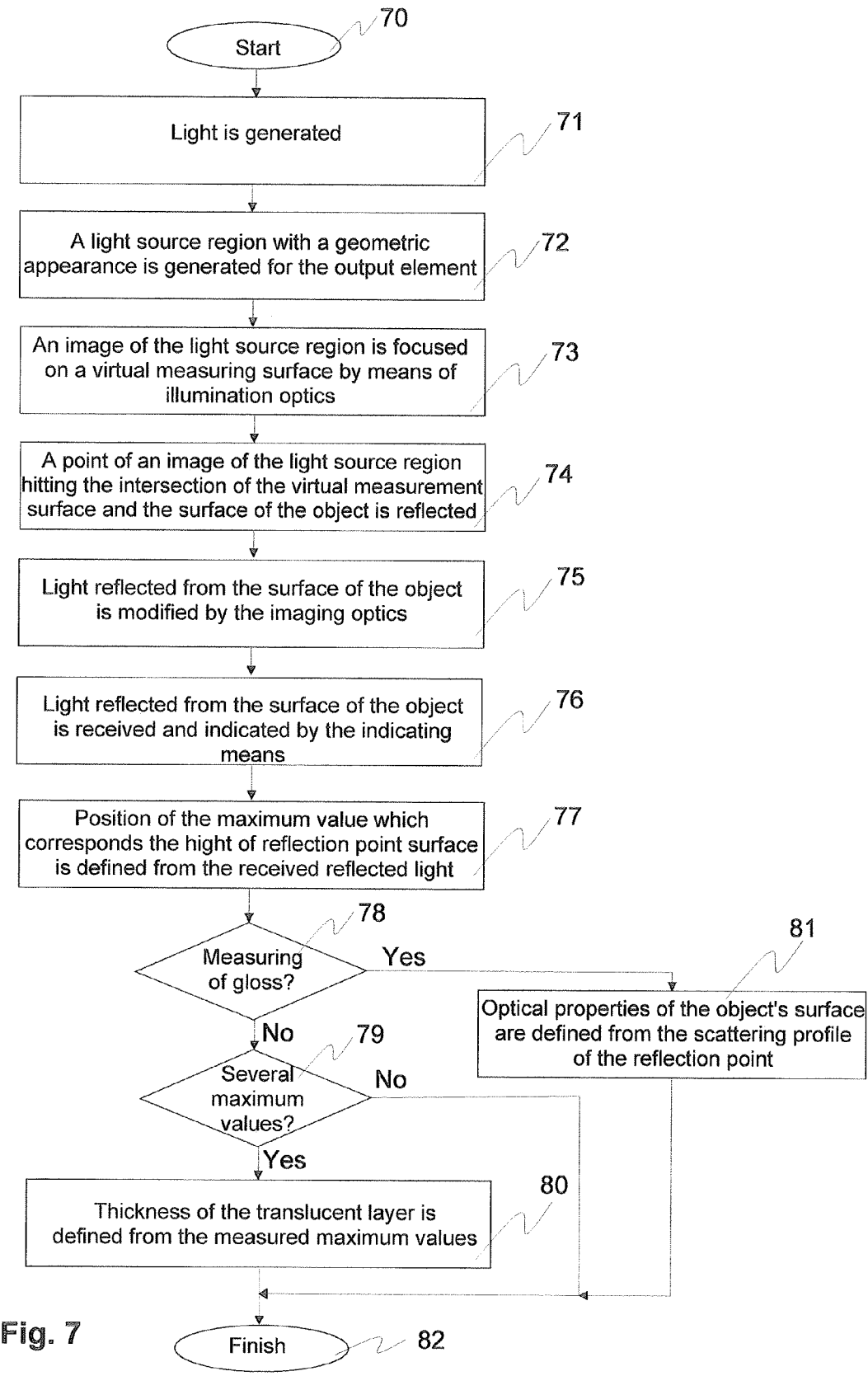

FIG. 2*a* shows by way of example realization in principle of a measuring device according to the first embodiment of the invention, FIG. 2*b* shows on the optical measuring device of FIG. 2*a* the measurement result of a transparent film, FIG. 2c shows by way of example realization in principle of a measuring device according to the second embodiment of the invention, FIG. 2c1 shows on the optical measuring device of FIG. 2c the measurement result of thickness of a transparent film, FIG. 2c2 shows a measurement result, obtained by an optical measuring device and describing optical properties of a film, FIG. 2d shows examples of light regions formed in the output element of the optical measuring device shown in FIG. 2a, FIG. 2e shows by way of example a measuring arrangement according to the invention where the focus planes of the illumination optics and imaging optics are directed to each other by inclining the output element and the input element FIG. 2f shows the simulation results of the optical measuring arrangement of FIG. 2e on a mirror surface and on a diffuse surface, FIG. 3 shows by way of example an optical realization in principle of a measuring device according to the third embodiment of the invention, where the focus regions are accomplished utilizing chromatic aberration, FIG. 4 shows by way of example an optical realization in principle of a measuring device according to the fourth embodiment of the invention, where the focus regions are accomplished utilizing spherical aberration, FIG. 5a shows by way of example a realization of an output element where a place-alternating linear variable filter is utilized, FIG. 5b shows by way of example an optical realization in principle of a measuring device according to the fifth embodiment of the invention, where a place-alternating linear variable filter is used both in illumination and imaging, FIG. 5c shows by way of example an optical realization in principle of a measuring device according to the fifth embodiment of the invention in a perspective view, FIG. 6a shows by way of example an optical realization in principle of a measuring device according to the sixth embodiment of the invention in a side view where both a place-alternating linear variable sensor and chromatic aberration are utilized, FIG. 6b shows by way of example an optical realization in principle of a measuring device according to the fifth or sixth embodiment of the invention and FIG. 7 shows by way of example main steps of the measuring method of the surface and optical properties of an object according to the invention.

DETAILED DESCRIPTION OF THE INVENTION

The embodiments in the following description are disclosed as examples only, and someone skilled in the art may realize the basic idea of the invention also in some other way than what is described in the description. Though the description may refer to a certain embodiment or embodiments in several places, this does not mean that the reference would be directed towards only one described embodiment or that the described characteristic would be usable only in one described embodiment. The individual characteristics of two or more embodiments may be combined and new embodiments of the invention may thus be provided.

In the following, some embodiments of the invention are disclosed where confocal measuring principle is utilized. In the described embodiments, illumination and imaging of the surface of the object is realized biaxially from different directions. Thus, a virtual measuring surface can be created onto which numerous focus points (measuring lines and/or groups of measuring points of focus points) that are common for said optics are created both by imaging optics and measuring optics. As the object to be measured intersects the virtual measuring surface, one focus point of the virtual measuring surface common for illumination and imaging optics hits said surface. Place of a strong reflection generated from this common focus point is indicated by a light sensor belonging to the imaging optics and converted to level data of the object.

FIG. 1a shows a structure of principle of a measuring arrangement according to the invention utilizing, confocal principle. In order to intersect the surface 2a of the object to be measured, onto a virtual measuring surface advantageously the geometric shape of the light source region is projected, and this image is monitored with receiver optics where the light distribution of the light reflected from the object to be measured is measured with a light sensor. In the light distribution of the light sensor, intensity maxims are created in those points that correspond to intersections of the surface of the target and the image of the light region projected onto the virtual measuring surface. Distance of the surface is determined from the place of the intensity maximum of the light distribution defined by the light sensor. If the surface consists of several partly light-permeable and reflecting surfaces, such as, for example, a plastic film or a glass plate, the method creates from these surfaces an individual intensity maximum, respectively, and the thickness of the film can be defined on basis of the difference between the positions of these intensity maximums.

The measuring arrangement 1 of FIG. 1a comprises optical transmitter parts 10 and 11 and optical receiver parts 12 and 13 drawn separately for clarity. For someone skilled in the art, it is obvious that the parts of the measuring device can form one or more aggregates instead of separate parts, whereby the measuring arrangement 1 is an optical measuring device.

The measuring arrangement 1 according to the invention comprises advantageously an optical illumination unit 10 that can comprise a separate light source and an optical output element for providing a light source region. The light source 10 is advantageously inclined by angle β in relation to the optical axis 11a of the illumination. The optical output element can be advantageously a slit or a reversal-film-like translucent mask. When light is directed to it light proceeds through the slit from the light source of the illumination unit 10. Image of the light source region where the shape of the output element or the intensity or wavelength distribution prepared by it, is distinguished, is created when the illumination optics 11 images 11b it into an image of the light source region onto the virtual measuring surface 3. Characteristics of the illumination optics 11, such as, for example, the area of incidence angle and magnification, determine further which features of the light region of the output element 102 are imaged onto the virtual measuring surface 3. The optical axis of the illumination optics is denoted with reference 11a.

The measuring arrangement 1 further comprises imaging optics 12 and imaging unit 13. The imaging unit 13 comprises advantageously an optical input element and a light sensor which can advantageously be a CCD sensor. The optical axis of imaging optics 12 is denoted with reference 12a. For the input element, onto the virtual measuring surface 3 by means of imaging optics 12 is imaged an image of the light source region formed by illumination optics 11. This imaging generated to the input element is shown with reference 12*b*.

By optical radiation in this application is meant electromagnetic radiation the wavelength band of which is located from ultraviolet radiation (wavelength ca. 50 nm) to infrared radiation (wavelength ca. 1 mm). The light source 10 can radiate depending on the application either white light (all visible wavelengths) or one or more wavelengths. The illumination optics 11 directs the optical radiation coming from the illumination unit 10 to the object to be measured such that the different parts of the light region formed by the optical output element 102 are focused at different heights onto the virtual measuring surface 3 intersecting the surface to be measured 2. Thereby, part of the formed points of the image of the light region can have their focus point directed above the surface of the object to be measured and part of them can have it directed inside the object (under the surface 2*a*).

By reflection is in this application meant a mirror reflection and diffuse reflection (scattering) where the reflection can occur from a smooth surface or a rough surface. Furthermore, by reflection in this application is meant also the radiation scattering, refracted and reflecting light from inside of the object to be measured.

Both the optical illumination means and optical imaging means of the measuring arrangement are configured to define the focus points of them both to the virtual measuring surface 3 such that the transmitter and receiver optics focus different points from the illumination and imaging area in a known way on the virtual measuring surface 3 to different positions. Thereby, there is always a corresponding point for each focus point created both by illumination optics and imaging optics on the measuring surface 3. When the surface 2 of the object to be measured is in a certain focus point of the virtual measuring surface 3, the reflection generated from it is very strong in comparison with the light reflected from other points of the surface 2. With the imaging optics 12, the light 12*b* reflected from the surface 2 of the object to be measured is formed and directed to the input element of the imaging unit 13, the position of the intensity maximum of the penetrated light being detected by the light sensor and the position data is formed into an electrical signal. The light sensor can be, for example, a CCD or CMOS matrix. From the imaging unit 13 the electrical signal of maximum reflection representing the level is advantageously directed to the presentation means (not shown in FIG. 1*a*) of the level, by which means the level of the measured surface 2*a* of object 2 is presented.

Example of FIG. 1*b* shows by way of example an advantageous embodiment of the invention realizing the FIG. 1*a*. FIG. 1*b* does not show the optical light source 10 that precedes the output element 100. The output element 100 is inclined by angle $\beta$ in comparison with the optical axis 11*a* of the illumination. The output element 100 can comprise one or more output slits. Points related with the extreme ends of the output slit are depicted with references $K_1(S)$ and $K_n(S)$. The illumination optics 110 images the output slit onto the virtual measuring surface 3 such that the point $M(k_1)$ corresponding the point $K_1(S)$ is in focus at the top end of the virtual measuring surface 3. Accordingly, the corresponding point $M(k_n)$ of point $K_n(S)$ is in focus at the bottom end of the virtual measuring surface 3.

The imaging optics 120 images the light reflected from surface 2*a*. The light sensor belonging to the imaging optics and included in the input element 130 is inclined by angle $\beta'$ in relation to the imaging axis. With this arrangement the imaging optics 12 is in focus on the virtual measuring surface 3 such that the point $M(k_1)$ is in focus only at the point $K_1(R)$ of the light sensor 130. Accordingly, the light sensor 130 has a corresponding point $K_n(R)$ for the point $M(k_n)$ of the virtual measuring plane 3. Thus, for each point of the light region of the output element 100 between $K_1(S) \rightarrow K_n(S)$ a corresponding point between $K_1(R) \rightarrow K_n(R)$ can be formed for the light sensor through the virtual measuring surface 3. When a certain pair of corresponding points hits the surface 2*a* of the object 2*a* strong reflection is created, the location of which is indicated by light sensor 130. The location is calibrated to indicate the height of the surface 2*a*.

FIG. 1*c* shows an example of measuring of the thickness of a not transparent object. The object comprises two surfaces the distance of which between each other is the thickness of the object at a certain position. In the example of FIG. 1*c*, the surface 2*a* is called top surface and the surface 2*b* is called bottom surface.

The top surface of the object is measured by the measuring arrangement 1 shown in connection with FIG. 1*a*, the measuring arrangement comprising the functional components described in connection with FIG. 1*a*.

The bottom surface 2*b* side of the object comprises another measuring arrangement 5. By its structure and operation it corresponds to the measuring arrangement 1. Thus, it comprises advantageously an optical light source 50 and an optical processing part of illumination, an optical part 51 of illumination, an optical part 52 of imaging, an optical processing part of imaging and detector means of imaging. Optical radiation emitted from the optical light source 50 is shaped with the optical part 51 to the measuring plane 53. Light produced by illumination is reflected at the measuring plane 53 from the surface 2*b* of the object. The reflected light is modified with the optical part 52 of imaging which modified reflected light is directed to the optical processing part 56 of the imaging where the light is altered further into an electrical signal. The electrical signal can be indicated by detecting means.

Thickness of a certain point of the object can be found out by combining the measuring results of the top and bottom surfaces of the detector means of the measuring arrangement 1 and measuring arrangement 5. The difference between the measuring results of the top and bottom surfaces corresponds to the thickness at the measuring point when the location data of the measuring plane of both measuring arrangements 1 and 5 is calibrated in three dimensions.

FIG. 2*a* shows by way of example the realization in principle of the measuring device utilizing confocal way of measurement according to the first embodiment of the invention. Both the illumination optics 11 and the imaging optics 12 are identical. In order to intersect the surface 2*a* of the object to be measured, a virtual measuring surface 3 is created with said optical means. In the example of FIG. 2*a* the measuring surface 3 is a plane that is perpendicular to surface 2*a*.

On the virtual measuring surface 3 certain parts of both the light source region of the illumination and the detector means of the imaging are in focus at the same positions.

The output element 100 of FIG. 2*a* is a plane with a linear output slit 102 or output slits. The point of the one extreme end of the output slit is denoted with reference $K_1(S)$ and the point of the other extreme end with reference $K_n(S)$. Direction of the output slit 102 is advantageously rotated to rotation angle $\alpha$ in respect of the plane defined by the optical axes of the illumination optics 11 and imaging optics, so that the image 31 of the output slit can be focused onto the virtual measuring surface 3, the direction of the image being in rotation angle φ in respect of the plane defined of the illumination optics 11 and imaging optics. Furthermore, the output element 100 is advantageously inclined into angle of tilt β in direction of the optical axis of the illumination optics, so that each point $K_1(S) \rightarrow K_n(S)$ of the output slit is able to be focused onto the virtual measuring surface as points $M(k_1) \rightarrow M(k_n)$.

In the imaging unit 13, the input slit or detector element 132 included in the input element 130 is rotated by a rotation angle α'. Furthermore, the input element 130 is inclined by an angle of tilt β' in direction of the optical axis of the imaging optics, whereby the image 31 formed by the illumination optics 11 from the light source region 102 onto the virtual measuring surface 3 can be focused with the imaging optics 12 to the input slit or detector element 132 into points $K_1(R) \rightarrow K_n(R)$ corresponding to the points $K_1(S) \rightarrow K_n(S)$ of the light source 102.

For the light sensor 132 of the imaging unit 13 a local maximum signal h01 is obtained from where the position of the surface 2a can be defined. The maximum signal comes to the input slit or detector 132 from position $h_0$, where the common, line image 31 intersects the surface 2a of the object to be measured at point $M(k_x)$. This intersection is imaged by the imaging optics 12 to the input slit or detector element 132 as point $K_x(R)$.

If the object 2 to be measured is at least partly of transparent material, in this case another strong reflected light signal arrives from surface 2b (not shown in FIG. 2a) to the input slit or detector element 132. The other maximum signal $h_1$ generated from the surface 2b hits a different position in the input slit 132 than the maximum signal $h_0$.

Advantageously, the rotation angle α' is not equal to zero. Thereby, the measuring arrangement can be used on both mirror and matte surfaces. If the rotation angle α' is zero, with it the distance of the surface to a diffuse surface can be measured that makes a clear narrow intensity maximum to the input slit or detector element 132. On a mirror-like surface, the width of the region of intensity maximum grows and it is not necessarily possible to define the maximum position accurately.

If the rotation angle α' is exactly 90 degrees, the measuring works only at one position of the height of surface. Light comes to the input slit or the detector element 132 only when the surface 2a is at the certain position $h_0$. At other heights of surface, there is no light coming to the input slit or detector element 132. With this angle of 90 degrees the method can be used to indicate when the surface is exactly at the certain position.

With the solution according to FIG. 2a, following technical advantages will be achieved. The illumination optics 11 forms a focused image 31 of the light source region 102, such as for example, of the output slits or LEDs, onto the virtual measuring surface 3, and simultaneously the imaging optics 12 is configured to image the image of the light source region being created onto the virtual measuring to the input slit or detector element 132. The measuring arrangement enables the fact that the depth of field of focus of the illumination and/or imaging can be arbitrary small, for example, micrometers, even if the region of level to be measured was, for example, ten millimeters.

Another technical advantage of the solution is that when using the output slit, luminous efficiency is directed to the created image 31 of the output slit from the whole angular space of the illumination optics 11 (=in numeric aperture, NA). In the same way, the imaging optics 12 collects light from the measuring points in a full angular region. Thereby, maximum luminous efficiency comes to the input slit or detector element 132, since a maximum angular space is available in illumination and imaging. In a solution according to the invention, a large angular space enables measuring of shiny surfaces in a large angular region. If, for example, both illumination and imaging would be performed in a way that the numeric apertures of the optics were very small, even a small change of angle of the surface of the object of the measurement would direct the light coming from the illuminator to be reflected past the receiver optics which would make the measuring impossible.

It is a technical advantage of the solution according to the invention that the measuring can be realized in a way that the illumination comes to the surface from a skew angle while the virtual measuring surface (measuring plane in FIG. 2a) remains still in a perpendicular angle in respect of the surface.

Further, an advantage of the invention is that measurement of the level of surface can be realized with one wavelength or several wavelengths.

FIG. 2b shows an example of a signal according to the first embodiment, received from the light sensor 132 of the measuring device in case of FIG. 2a. FIG. 2b shows the intensity of the light coming to the input slit or detector element 132 as a function of a position of the detector element. The first maximum signal $h_0$ is caused by a reflection from the surface 2a of the object 2. The second maximum signal $h_1$ is a result of a reflection coming from the surface 2b of the object 2. The second reflection $h_1$ is of smaller size than the first reflection $h_0$, since the light has had to travel through material 2 where part of the energy of the light has absorbed. From the difference of the positions of the maximum signals $h_0$ and $h_1$ the thickness of the object 2 at the measuring point can be defined when the refractive index of the material is known. The intensity distribution shown in FIG. 2b can be measured, for example, by placing a multi-element light sensor directly behind the input slit 132 or by imaging the input slit 132 with optics to the multi-element sensor. The input slit can also be replaced by, for example, a multi-element line sensor of the same shape, whereby a separate input slit is not necessary.

FIG. 2c shows a measuring arrangement according to the second embodiment of the invention. The measuring arrangement differs from the measuring arrangement of FIG. 2a in that the input element 130a comprises a matrix detector 132a. With a matrix detector 132a it is possible to simultaneously measure the intensity of the reflected light in vertical direction of the surface 2a, points $K_1(R) \rightarrow K_n(R)$, and the intensity of the reflected light in an angle of 90 degrees against the detection axis of vertical direction of the surface of the object 2, points $P_1(R) \rightarrow P_n(R)$. This intensity distribution represents the optical properties of the surface of the object 2.

FIG. 2c1 shows positions $h_0$ and $h_1$ of (at least partly translucent) two surfaces 2a and 2b of the object 2.

FIG. 2c2 shows the intensity distribution measured at the surface 2 in the second measuring direction. The optical properties of the surface 2a of the object have an effect on the shape of the intensity distribution $h_0$. The internal structure and interfaces of the object 2 and the optical properties of the surface 2b have an effect on the shape of the intensity distribution $h_0$.

FIG. 2d shows exemplary technical realizations of the output element 100 or the input element 130. FIG. 2d shows exemplary output or input elements with one or more output or input slits.

FIG. 2e shows an example of a measuring device where the output element 100 forms an angle of 135 degrees with the optical axis of the illumination optics 11 and where the input element 130 forms, correspondingly, an angle of 135 with the optical axis of the imaging optics 12. The magnification of both the illumination optics 11 and the imaging optics 12 is 1. With this arrangement, the light region of the output element 100 and the detector element of the input element 130 are provided to have common corresponding points on the virtual measuring surface 3.

FIG. 2f shows the simulation results on the detecting element of the measuring device according to FIG. 2e in two different cases, on a mirror-like surface and on a diffuse surface.

In case of a mirror-like surface, on the axis of height of surface (direction A-B) a clear maximum value, position signal was obtained at a point where the virtual measuring plane 3 intersects surface 2a of the object 2. Direction A-B in FIG. 2f corresponds to the measuring direction of the axis of height of surface on the detector element 132 in FIG. 2c. In case of a mirror surface, the intensity distribution of light measured substantially in an angle intersecting in respect of the axis of height of surface (direction C-D) at the above-mentioned maximum point is relatively strong and wide. In an advantageous embodiment the intersecting angle can be 90 degrees compared to the axis of height of surface. The optimal value of the intersecting angle depends advantageously at least on the angle α of the output slit on the output element.

If the surface 2a of the object 2 is diffuse, also then further a strong position signal is obtained at a point where the virtual measuring plane 3 intersects the surface 2a of the object 2. In case of a diffuse surface, the intensity distribution of light measured in an angle intersecting in respect of the axis of height of surface at the above-mentioned maximum point is narrow and clearly smaller than in case of the mirror surface. Furthermore, the shape of the intensity distribution differs clearly from the intensity distribution given by the mirror surface. By measuring the value of one or more points included in the intensity distribution the gloss characteristics of the surface 2a of the object can be defined.

FIG. 3 shows a second advantageous embodiment of the invention where the output slit 102 and input slits or light sensor 132, 132a and chromatic aberration are utilized. Thanks to the chromatic aberration, the images of the output slit 102 in wavelengths $\lambda_1(S)$, $\lambda_n(S)$ and the images of the input slit 132 in wavelengths $\lambda_1(R)$, $\lambda_n(R)$ are formed at different distances from optics 111 and 121, whereby the output element 100 and the light sensor 132 and 132a need not to be inclined in respect of the axes 11a and 12a of the illumination optics 111 or imaging optics 121 (angles β and β'=90), but the image planes meet each other on the virtual measuring surface 3 in the same wavelengths $\lambda_1(S)$, $\lambda_1(R) \rightarrow \lambda_n(S)$, $\lambda_n(R)$. Thereby, the output element 100 and the light sensor 132 can be in a perpendicular angle in respect of the optical axis which is advantageous from the point of view of the structure of the device.

In this embodiment, the light is generated advantageously by a LED radiating white light (not shown in FIG. 3), whereby light with sufficient wideband is obtained as to its wavelength distribution, the different wavelengths of which can be focused at different distances in direction of the optical axis.

In the example of FIG. 3, in the output element 100 one exemplary output slit is shown. In the left upper edge of FIG. 3, the position of the output slit 102 in the output element 100 is shown viewed in the direction of the optical axis of the illumination optics 111. The output slit 102 is rotated by a rotation angle α in regard of the plane defined by the optical axes of the illumination optics 111 and the imaging optics 121.

In an advantageous embodiment of the invention, the cylindrical illumination optics 111 flattens down the image of the output element 100 in relation x=1 and y=0.2.

By illumination optics 111 is produced an axial, chromatic aberration. Thereby, in the example of FIG. 3, the components $\lambda_n(S)$, $\lambda_n(R)$ of the red end of the light are in focus on the virtual measuring surface 3 under the surface 2 of the object, and, correspondingly, the components $\lambda_1(S)$, $\lambda_1(R)$ of the blue end of the light are in focus above the surface 2a.

In the example of FIG. 3, both the blue ends $\lambda_1(S)$, $\lambda_1(R)$ of the illumination and imaging are in focus in the upper edge of the virtual measuring surface 3. Accordingly, the red ends $\lambda_n(S)$, $\lambda_n(R)$ of the spectra are in focus in the bottom edge of the measuring surface (under the surface 2a in FIG. 3). The height of the surface 2a has an effect on which component of the spectrum is reflected from the surface 2a. The colour of the component of the spectrum is not important in this embodiment, since the light signal reflected from surface 2a is detected advantageously by a black and white line or matrix sensor/camera 132, 132a. Also in this embodiment, the position of surface 2a is indicated by the position of the maximum of the received signal on the sensor of the camera working as the indicator. The position of the received maximum signal is calibrated to correspond to a certain height of the surface 2a.

In the example of FIG. 3, both the illumination and imaging are shown in a symmetrical angle in regard of the surface 2a. The invention is however not restricted to this kind of a symmetrical measuring situation, but the edge of the illumination and imaging in regard of the surface 2a can be of different size without having an effect of the measuring event. Although the angle between illumination and imaging changes, nevertheless, in overlapping measuring regions there can always be found on measuring line where individual focus points can be found for different wavelengths.

There are several advantageous technical effects of this embodiment. For example, change of focal length of the wavelength (drift) caused by temperature does not have an effect on the measuring result. If the temperature drifts of the illumination and the imaging optics and the chromatic aberration are equal, the position of the measuring surface remains constant with changing temperature, and the illumination and imaging remain in focus on the measuring surface on the same wavelength with each other.

Further, in this embodiment, the light sensor 132 or 132a of the imaging optics can be vertically against the optical axis 12a of the imaging optics. Thus, the size and shape of the measuring region can be freely defined with the used illumination and imaging optics. For example, in imaging the size of the measuring region can advantageously be enlarged for the measuring sensor of the matrix camera.

FIG. 4 shows the third advantageous embodiment of the invention whereby in providing confocality, spherical aberration is utilized. FIG. 4 shows further an example of the meaning of spherical aberration. An exemplary lens 112 or 122 refracts the light to different focus points $\Theta_1(s)$, $\Theta_n(s)$ and $\Theta_1(R)$, $\Theta_n(R)$ on the grounds that where the light penetrates the lens 112 or 122. Light beams penetrating the lens at the centre have their focus point $\Theta_n(S)$, $\Theta_n(R)$ further away than the light beams penetrated on the outer edges of the lens.

In the embodiment of FIG. 4, the height measuring is based on the spherical aberration of the lens or lenses and on the confocal imaging. The spherical aberration used is advantageously of the same size in imaging and in illumination. Thereby, signals having the same angular aperture are imaged onto the measuring plane in direction of the normal of the surface. In this embodiment, the measuring can be realized either with one wavelength or white light.

The spherical aberration makes the optics to image the output slit in the output element 100 at different distances depending on the angular aperture of the optics. For example, light beams coming to a large angular aperture form an image close to the imaging optics 112, and accordingly, beams coming to a small incident angular aperture form an image farther away from the imaging optics 112. Thereby, the output element 100 and the light sensor 132 need not to be inclined in relation to the axes 11*a* and 12*a* of the illumination optics or imaging optics (angles β and β'=90), but the image planes meet each other on the virtual measuring surface 3 with equal angular apertures of the optics. Thereby, the output element 100 and the light sensor 132 can be in a perpendicular angle in respect of the optical axis which is advantageous from the point of view of the structure of the device.

In the embodiment of the invention shown in FIG. 4, in addition to spherical aberration, the output slit 102 and light sensor 132 or 132 are utilized. Thanks to the spherical aberration, the image of output slit 102 on the virtual measuring surface 3 is formed at different distances with different angular apertures $\Theta_1(S)$, $\Theta_n(s)$. Accordingly, the imaging optics 122 comprises the same property. Thereby, the output element 100 and the light sensor 132 need not to be inclined in relation to the axes 11*a* and 12*a* of the illumination optics 111 or imaging optics 121, but the image planes meet each other on the virtual measuring surface 3 with equal angular apertures $\Theta_1(s)$, $\Theta_1(R)$ and $\Theta_n(S)$, $\Theta_n(R)$. Thereby, the output element 100 and the light sensor 132 can be in a perpendicular angle in respect of the optical axis which is advantageous from the point of view of the structure of the device. Also in this embodiment, a certain point of the light sensor 132 of the imaging unit is calibrated to correspond to a certain height of surface 2*a*.

FIG. 5*a* shows an exemplary embodiment of the output or input element 100 or 130, whereby a linear variable filter 102 is utilized. A linear variable filter, also known by LVF (Linear Variable Filter), lets at certain positions only a certain wavelength $\lambda_1$, $\lambda_2$, $\lambda_n$ go through. Thus, each wavelength has on own, narrow output slit in a different position, the image of which can be focused with imaging optics 11 onto the virtual measuring surface 3.

FIG. 5*b* shows the fourth advantageous embodiment of the invention, where in providing confocality a linear variable filter (LVF) is utilized both in illuminating and imaging. A LVF filter lets at different parts different wavelengths go through. At the one end of a LVF filter, shorter wavelengths are allowed to pass through, and at the other end, longer wavelengths can pass through.

The light source of the illumination has to be a light source with a sufficient wideband as to its wavelength distribution (not shown in FIG. 5*b*), in order to be able to focus different wavelengths $\lambda_1(S) \to \lambda_n(S)$ with illumination optics 113 to different positions onto the virtual measuring surface 3. From an image created onto the virtual measuring surface 3, with imaging optics 123 is obtained from surface 2*a* to the light sensor 132 a local maximum signal, from which the distance to surface 2*a* can be defined.

In this embodiment, the output element 100 comprises a position-dependent linear variable filter 102*a* that comprises wavelengths $\lambda_1 \to \lambda_n$. An image of the LVF filter is obtained in focus onto the virtual measuring surface 3 by inclining the output element 100 by angle β in relation to the optical axis 11*a* of the illumination optics 113. The angle β can advantageously be, for example, 135 degrees, whereby the focus region of the illumination hits the virtual measuring surface 3.

The light sensor 132 is advantageously of linear or rectangular shape, having in front of it as an input element a position-sensitive linear variable filter 102*a*. The LVF filter 102*a* also comprising the wavelengths $\lambda_1 \to \lambda_n$, is inclined in respect of the optical axis 12*a* of the imaging optics by an angle β', so that its image $\lambda_1(R) \to \lambda_n(R)$ joins the plane of the image projected from the output element 102*a* onto the virtual measuring surface 3. The angle β' can advantageously be, for example, 135 degrees, whereby the focus region of the illumination hits the virtual measuring surface 3.

FIG. 5*c* shows the measuring arrangement of FIG. 5*b* in a perspective view. The different wavelengths $\lambda_1 \to \lambda_n$ of the LVF filter included in the output element are shown viewed from direction of the optical axis 11*a* of the illumination. Accordingly, the different wavelengths $\lambda_1 \to \lambda_n$ of the LVF filter 102*a* belonging to the output element are shown viewed from the direction of the optical axis 12*a* of the imaging.

With the measuring device according to this embodiment, the measuring of the level of the height of the profile 2*h*0 can be realized. The method produces the measuring result 132$h_0$ of the surface, height profile of the surface, for the matrix detector 132*a* from the output element of the imaging for the width of the image projected to the object 2. Thus, by the measurement, for example, a measurement of surface height profile of 1 000 pixels can be realized by using a CCD image sensor in size of 1 000×1 000 pixels as a light sensor.

FIG. 6*a* shows the fifth advantageous embodiment of the invention in a side view. In this embodiment of the invention, in providing confocality, a linear variable filter (102*a*) is utilized both in the illumination and imaging. Further, chromatic aberration is provided in the illumination optics 114 and imaging optics 124. Also in this embodiment, a local maximum signal is obtained for detector 132*a*, from which the distance to surface 2*a* can be defined.

As an output element advantageously a position-dependent linear variable filter 102*a* is utilized. In the illumination optics 114 and the imaging optics 124 a chromatic axial aberration of suitable size is provided, by means of which the image of the LVF filter 102*a* of the output element and the image of the LVF filter in front of the light sensor 132*a* of the imaging optics 124 is brought into focus by wavelengths on the virtual measuring surface 3. The angle of inclination β can thereby be 90 degrees. Accordingly, the angle of inclination β' of the input element can thereby be 90 degrees, which makes the positioning of the light sensor 132*a* and the imaging optics 124 easier in relation to each other.

In the example of FIG. 6*a*, the blue ends (λ) of the spectra of both the illumination and imaging are in focus in the upper edge of the virtual measuring surface 3. Accordingly, the red ends ($\lambda_n$) of the spectra are in focus in the bottom edge of the virtual measuring surface 3 (below the surface 2*a* in FIG. 6*a*). The height of the surface 2*a* has an effect on which wavelength of the spectrum is reflected from the surface 2*a*. When a wavelength is reflected from the surface 2*a* that is in the common focus point of both the illumination and the imaging, this reflected wavelength penetrates the LVF filter 102*a* in front of the light sensor 132*a* only at one position. The position of the component of the spectrum penetrated the LVF filter 102a is indicated, for example, by a black and white matrix camera 132a. Also in this embodiment, the position of the surface 2a is indicated by the position of the received maximum signal on the light sensor 132a and not the wavelength of the received spectrum. The position of the received maximum signal on the light sensor 132a is calibrated to correspond to a certain height of the surface 2a.

With the measuring device according to this embodiment, the measuring of the surface height profile can be realized. A measuring device according to this embodiment produces a distance measurement result at the whole width of the image projected from the output slit to the object. Thus, by the measurement, for example, a measurement of a distance profile of 1 000 pixels can be realized by using a CCD image sensor in size of 1 000×1 000 pixels as a light sensor.

FIG. 6b shows exemplary illumination optics 114 or imaging optics 124, a LVF filter 102a and a light source 10 or light sensor 132a, by which the embodiment of the invention according to FIG. 6a can be realized. In the frame 580 of the optics, three lenses 581, 582 and 583 are mounted, by which both the axial chromatic aberration and the magnifications of lenses in direction of axes x and y are produced. By reference 585 an opening is indicated, against which the LVF filter 102a is fastened.

If it comes to the illumination optics 114, then in front of the LVF filter 102a there is, for example, a LED light source 10 emitting white light. The light of the LED passes through the LVF filter 102a such that the different wavelengths of the white light get through only at certain positions in the LVF filter. Lenses 581, 582 and 583 modify the light A dispersed into different wavelengths of the spectrum passed through the LVF filter such that the result is an axial, chromatic aberration.

If it comes to the imaging optics 124, then behind the LVF filter 102a there is a light sensor 132a that may be a conventional CCD measuring sensor. The certain wavelength of the light B reflected from the surface 2a passes through the LVF filter 102a such that it penetrates the LVF filter 102a only at a certain position. This position of penetration of the wavelength is indicated by the CCD sensor. In the measuring arrangement the certain position of the CCD sensor is calibrated to indicate a known height of the surface 2.

The LVF filter shown in FIG. 6b can be, for example, of type JDSU LVF4007003A, the filtering range of which is 400-700 nm. Dimensions of the filter are 12.5×5.4×1.5 mm (length; width; height). The bandwidth of 3 dB of this LVF filter is in the range of 10 nm.

FIG. 7 shows in an exemplary flow chart main phases of the inventive measuring method.

In a step 70 preceding the measuring, the equipment belonging to the measuring arrangement are mounted into the object of measurement. At the same time the focus regions of both the illumination optics and the imaging optics are aligned with each other. At the same time, advantageously, it is defined or calibrated which height of surface is represented by the received position of the maximum signal in the measuring sensor. As the measuring equipment is in its location of measurement and calibrated for the measurement, it is proceeded to the actual measuring process.

In step 71, the light to be utilized in the measuring arrangement is generated. The light can be either monocromatic or wideband, for example white, light depending on the embodiment. As a light source, usually either a LED emitting one wavelength or a LED emitting white light is used.

In step 72, in measuring, a light source region is generated for the output element 100 of the illumination that has an optimal geometric appearance from the point of view of the object of the measuring. In an advantageous embodiment of the invention, this means guiding the light through an inclined grated structure. The grated structure is provided by slits 102 made in the plane. In this embodiment, from each slit of the grate one optical measuring signal is created that can be directed to the measuring plane that is substantially in the direction of the normal of the surface of the object of measurement.

In another advantageous embodiment of the invention, in this step 72, white light is utilized that is directed to the LVF filter 102a. In this embodiment, the white light is dispersed into a spectrum with the LVF filter, and the dispersed spectrum is directed to a measuring plane in direction of the normal of the surface of the object of measurement.

In step 73, the image of the light source region 102, 102a created in step 72 is modified by the illumination optics. As the end result of modification, a virtual measuring surface 3 substantially intersecting the surface 2 to be measured, or a known group of focus points representing it, is provided.

In step 74, the image of the light source region modified by the illumination optics hits the surface 2 being the object of the measurement. Since the focus points formed by the illumination optics are on the virtual measurement surface 3, only one of the possible focus points hits the surface 2a to be measured, as the virtual measurement surface 3 intersects the surface 2a being the object of the measurement. From this focus point a light beam is reflected, the intensity of which is much higher than the light reflecting from the other locations of the surface 2a onto the imaging optics, since also the imaging optics has one focus point in the reflection point.

In step 75, the light beam is imaged from the surface 2a with the imaging optics onto the used position measuring means. The imaging optics is such that only the points on the virtual measuring surface 3 are in focus also on the detector means 130, 130a utilized in the imaging.

In an advantageous embodiment of the invention, the imaging optics comprises also a LVF filter 102a that can advantageously be utilized also as position indicating means.

In step 76, the light reflected from the surface 2a is received either with a line detector 132, a matrix detector 132a, a black and white camera or a colour camera.

In step 77, the position of the maximum value is defined from the received reflected light by detector means 132, 132a. Each individual position of maximum value on the detector means is calibrated to correspond a certain distance of the surface.

In step 78, it is checked whether also the optical properties of the surface 2a of the object 2 are measured. If other optical properties are not measured the process proceeds to step 79.

In step 79, it is checked whether there are several individual maximum values indicated from the light reflected from the received object 2. If there is only one maximum value, the measured value represents the distance of the surface being the object of the measurement.

If there are found two or more maximum values in step 79, then in step 80, the distance of the reflection points from the surface is defined. In this case, it comes to a translucent film-like structure consisting of one or more material layers.

In this case, the first indicated maximum value represents the height of the upper surface of the film and the last indicated maximum value represents the height of the bottom surface of the film. If there are more than two maximum values, each of the other indicated maximum values represents an interface reflecting light inside the material to be measured. From the positions of the indicated maximums the thickness of each layer belonging to the film structure can be calculated. If a partly translucent material does not include obvious separate films but is in its nature, for example, a diffusely scattering material, the signal produced by the method produces information about the intensity of light scattering from different depths. An object of measurement of this type could be, for example, skin.

If it is found in step 78 that also the optical properties of the object 2 are being measured, then it is proceeded to step 81. In step 81, the scattering characteristics of the surface 2a are measured. The scattering characteristics are found out by measuring at the maximum reflection position that indicates the position of the surface also the intensity profile in one or more points in direction intersecting in relation to the position axis. The measured points included in the intensity profile of the light in this direction are proportional to the scattering characteristics of the surface 2a of the object 2. When the scattering characteristics of the object 2 are defined, the measuring process proceeds to step 82. In an advantageous embodiment of the invention, in the vicinity of the maximum reflection point caused by the surface the intensity profile of the light is measured as some kind of a regional profile.

An individual measuring process of the height of the surface ends in step 82. It is obvious for someone skilled in the art that the measuring process can return back to step 71 whereby a continuous measuring process is produced.

Above some advantageous embodiments of the method and the device according to the invention are described. The invention is not limited to the solutions described above, but the inventive idea can be applied in numerous ways within the scope of the claims.

The invention claimed is:

1. A measuring device for defining a position and optical properties of a surface of an object (2) by use of optical radiation, the measuring device comprising:
   an optical light source the produces light;
   illumination optics that direct the light produced by the optical light source to the surface of the object to be measured;
   an imaging unit (13); and
   imaging optics that are configured to collect reflected or scattered light from the object to be measured to the imaging unit (13), wherein,
   the imaging unit (13) is configured to measure the light and indicate an intensity distribution of the light coming, via the imaging optics, from the object of measuring,
   the optical light source includes an optical output element comprising one or more line-like optical output elements or one or more point-like optical output elements that produce the light of the optical light source at least in one wavelength,
   the imaging unit comprises an input element that includes a light sensor comprised of one or more line-like, point-like or region-like detector areas that include only one corresponding detector point (K1(R)→Kn(R)) for each individual point (K1(S)→Kn(S)) of the optical output element of the optical light source, the imaging unit being configured to measure the light and define intensity values of the light at least for a part of the corresponding detector points (K1(R)→Kn(R)) of the detector area and to define a location of the surface to be measured from the position of the maximum intensity of light (Kx(R)) in the detector area, and
   the illumination optics and the imaging optics are configured to form a common focus point on a virtual measuring surface such that on the virtual measuring surface an image formed by the illumination optics from points (K1(S)→Kn(S)) of the optical output element of the optical light source is overlapping with an image formed by the imaging optics from the corresponding points (K1(R)→Kn(R)) of the detector area at least in one common wavelength (λ) or angular aperture (Θ) of the illumination optics and the imaging optics.

2. The measuring device according to claim 1, wherein the measuring device further comprises a matrix detector for defining a gloss degree or optical properties of the surface of the object to be measured in an area surrounding the area of maximum intensity indicating the position of the surface of the object to be measured from a distribution of the intensity values ($P_1(R)$, $P_n(R)$) of the measured light.

3. The measuring device according to claim 2, wherein, in the illumination optics and the imaging optics, a longitudinal chromatic aberration is provided such that the image formed by the illumination optics from the output slits and the image formed by the imaging optics from the detector area are overlapping in the virtual measuring plane at least on some common wavelength ($λn(S)$, $λn(R)$) as it comes to their corresponding points.

4. The measuring device according to claim 2, wherein, in the illumination optics (11) and the imaging optics, a spherical aberration is provided such that the image formed by the illumination optics from the output slits and the image formed by the imaging optics from the detector area are overlapping in the virtual measuring plane at least on some common angular aperture ($θ_n(S)$, $θ_n(R)$) as it comes to their corresponding points.

5. The measuring device according to claim 1, wherein the virtual measuring surface is one of the following: a plane, a curved surface, a line, a set of lines or a group of dots.

6. The measuring device according to claim 1, wherein,
   the optical output element of the optical light source comprises one or more line-like output slits that form a rotation angle (α) with the plane defined by an optical axis of the illumination optics, and an optical axis of the imaging optics, and
   said rotation angle (α) is 0-90 degrees.

7. The measuring device according to claim 6, wherein, the optical light source forms an angle of inclination (β) to the optical axis of the illumination optics, and by said angle of inclination (β), the illumination optics is configured to focus the image of the output slits onto the virtual measuring surface.

8. The measuring device according to claim 1, wherein, in the illumination optics and the imaging optics, a longitudinal chromatic aberration is provided such that the image formed by the illumination optics from the output slits and the image formed by the imaging optics from the detector area are overlapping in the virtual measuring plane at least on some common wavelength ($λ_n(S)$, $λ_n(R)$) as it comes to their corresponding points.

9. The measuring device according to claim 1, wherein, in the illumination optics and the imaging optics, a spherical aberration is provided such that the image formed by the illumination optics from the output slits and the image formed by the imaging optics from the detector area are overlapping in the virtual measuring plane at least on some common angular aperture $(\theta_n(S), \theta_n(R))$ as it comes to their corresponding points.

10. The measuring device according to the claim 1, wherein,
the optical light source forms an angle of inclination ($\beta$) to the optical axis (11a) of the illumination optics,
the optical output element of the optical light source produces it wideband light and the optical output element comprises a position-depending linear variable filter,
the detector area further comprises a position-depending linear variable filter, the corresponding points of the detector area having the same wavelength ($\lambda_1, \lambda_n$) of passband as the corresponding points of the linear variable filter of the light source area, and
the output element is inclined to the angle of inclination ($\beta$) formed in relation to the optical axis of the illumination optics, and also the detector area is inclined to a corresponding angle of inclination ($\beta'$) such that a point of the linear variable filter of the optical output element and the corresponding point of the linear variable filter of the light sensor have a common focus point on the virtual measuring surface on same mutual wavelengths $(\lambda_n(S), \lambda_n(R))$.

11. The measuring device according to the claim 1, wherein,
the optical output element of the optical light source produces non-monochromatic light and the optical output element comprises a position-depending linear variable filter
the input element further comprises a position-depending linear variable filter, the corresponding points of which having the same wavelength ($\lambda_1, \lambda_n$) of passband as the corresponding points of the linear variable filter of the optical output element, and
in the illumination optics and the imaging optics, a longitudinal chromatic aberration is provided such that the point of the linear variable filter of the optical output element and the corresponding point of the linear variable filter of the input element (130) have a common focus point on the virtual measuring surface on same mutual wavelengths ($\lambda n(S), \lambda n(R)$).

12. The measuring device according to claim 1, wherein the light sensor is a line scan camera, a matrix camera or a mass center detector of light.

13. The measuring device according to claim 1, wherein, when measuring an optically transparent object each internal or external interface of the object produces a separate maximum signal ($h_0, h_1$), from the difference of which the measuring device is configured to determine a thickness of the transparent object.

14. The measuring device according to claim 13, wherein, from an intensity distribution of the light scattered/scattering from the inside of the object it is configured to be determined an inner structure of the object from the intensity of the light scattered at different depths.

15. A measuring arrangement for measuring a thickness of an object to be measured, comprising a first measuring device for measuring a first surface and a second measuring device for measuring a second surface, wherein both the first and second measuring devices correspond to claim 1 and the first measuring device is configured to measure a height of a top surface of the object, and the second measuring device is configured to measure a height of a bottom surface) of the object, and that a difference between the measurement results is configured to be indicated in a measurement arrangement as a thickness of the object.

16. A method of measuring optically a height of surface of an object, whereby an optical illumination and an optical imaging of the surface of the object is performed biaxially with at least one wavelength such that both illumination and imaging are directed to the surface from different directions, wherein the imaging and the illumination are realized confocally onto a virtual measuring surface that intersects the surface of the object, and a level of the object is indicated at the position ($K_x(R)$) of intensity maximum of the light distribution of the light reflected from the surface of the object, received by an imaging unit in an image sensor of the imaging unit that includes only one corresponding point ($K_1(R) \rightarrow K_n(R)$) for each individual point ($K_1(S) \rightarrow K_n(S)$) of the optical output element of the optical light source.

17. The method according to claim 16, wherein, an optical light pattern is created by illuminating one or more line-like output slit, the image produced by them being modified by illumination optics such that different parts ($K_1(S), K_n(S)$) of a light pattern created by the output slits are in focus on the virtual measuring surface at different positions.

18. The method according to claim 17, wherein, the illumination optics focuses the optical light pattern created by the output slits onto the virtual measuring surface either by chromatic aberration or spherical aberration.

19. The method according to claim 17, wherein, in order to achieve confocality, the imaging optics images a reflection point generated at the intersection of the image of the output slit on the virtual measuring surface and the surface of the object by the input element onto one detector element by using either chromatic aberration or spherical aberration.

20. The method according to claim 16, wherein, non-monochromatic light is filtered with a position-depending linear variable filter before the illumination optics and the image of the output slit (102a) created by the position-depending linear variable filter, imaged by the illumination optics onto the virtual measuring surface and a light wavelength ($\lambda_1, \lambda_n$) reflecting from an intersection of the surface of the object are imaged through a position-depending linear variable filter after the imaging optics onto one detector element.

* * * * *